(12) United States Patent
O'Grady et al.

(10) Patent No.: US 7,811,553 B2
(45) Date of Patent: Oct. 12, 2010

(54) MOLDED SHAVING AID COMPOSITIONS, COMPONENTS AND METHODS OF MANUFACTURE

(75) Inventors: Janet Kelley O'Grady, Westwood, MA (US); Marilyn Jeanne Westgate, Belmont, MA (US); Corey E. Corbeil, Attleboro, MA (US); Robert Harold Johnson, Melrose, MA (US); Maureen Sullivan Morrissey, Belmont, MA (US); Yun Xu, Langhorne, PA (US); Gregory Thomas Danti, Lynnfield, MA (US); John Anderson, North Andover, MA (US); Michael John Moloney, Brimfield, MA (US); Robert Houlihan, Jackson, NH (US)

(73) Assignee: The Gillette Company, Boston, MA (US)

( * ) Notice: Subject to any disclaimer, the term of this patent is extended or adjusted under 35 U.S.C. 154(b) by 674 days.

(21) Appl. No.: 11/595,490

(22) Filed: Nov. 8, 2006

(65) Prior Publication Data

US 2007/0110703 A1    May 17, 2007

Related U.S. Application Data

(60) Provisional application No. 60/735,758, filed on Nov. 9, 2005.

(51) Int. Cl.
  *A61Q 9/02* (2006.01)
  *A61Q 5/12* (2006.01)
  *A61K 31/74* (2006.01)
  *B26B 21/00* (2006.01)

(52) U.S. Cl. .................. 424/73; 424/70.12; 424/78.02; 30/32

(58) Field of Classification Search .................. None
  See application file for complete search history.

(56) References Cited

U.S. PATENT DOCUMENTS

| | | | | |
|---|---|---|---|---|
| 4,398,045 A | * | 8/1983 | Sebag | ................... 568/624 |
| 4,474,683 A | * | 10/1984 | Story et al. | .................. 510/445 |
| 4,850,106 A | | 7/1989 | Braun et al. | |
| 5,262,154 A | * | 11/1993 | Wendel et al. | ................. 424/73 |
| 5,345,680 A | | 9/1994 | Vreeland et al. | |
| 5,349,750 A | | 9/1994 | Tseng | |
| 5,431,906 A | * | 7/1995 | Mohseni et al. | ................ 424/73 |
| 5,560,859 A | | 10/1996 | Hartmann et al. | |
| 5,653,970 A | | 8/1997 | Vermeer et al. | |
| 5,741,509 A | | 4/1998 | Kushner et al. | |
| 5,956,849 A | | 9/1999 | Chadwick et al. | |
| 5,972,320 A | | 10/1999 | Moloney et al. | |
| 6,216,345 B1 | | 4/2001 | Andrews et al. | |
| 6,231,845 B1 | * | 5/2001 | Morrissey et al. | ............. 424/73 |
| 6,584,690 B2 | | 7/2003 | Orloff et al. | |
| 6,948,249 B2 | | 9/2005 | Barone et al. | |
| 6,993,846 B2 | | 2/2006 | Orloff | |
| 6,996,908 B2 | | 2/2006 | Orloff et al. | |
| 7,043,841 B2 | | 5/2006 | Franzini et al. | |
| 7,069,658 B2 | | 7/2006 | Tseng | |
| 7,086,159 B2 | | 8/2006 | Motta et al. | |
| 7,127,817 B2 | | 10/2006 | Orloff et al. | |
| 7,162,800 B2 | | 1/2007 | Orloff et al. | |
| 2003/0082218 A1 | * | 5/2003 | Ichinohe et al. | ............. 424/401 |
| 2003/0200659 A1 | | 10/2003 | Coffin et al. | |
| 2003/0200660 A1 | | 10/2003 | Pennella et al. | |
| 2003/0200661 A1 | | 10/2003 | Okada | |
| 2004/0208915 A1 | | 10/2004 | Abbott et al. | |
| 2005/0011073 A1 | | 1/2005 | Sandor et al. | |
| 2005/0015990 A1 | | 1/2005 | Barone et al. | |
| 2005/0028370 A1 | | 2/2005 | Pennella et al. | |
| 2005/0066526 A1 | | 3/2005 | Guimont et al. | |
| 2006/0008038 A1 | | 1/2006 | Song et al. | |
| 2006/0225285 A1 | | 10/2006 | Slavtcheff et al. | |

FOREIGN PATENT DOCUMENTS

| | | |
|---|---|---|
| WO | WO 92/15278 A1 | 9/1992 |
| WO | WO 01/65964 A2 | 9/2001 |
| WO | WO 01/89464 A1 | 11/2001 |
| WO | WO 03/090983 A1 | 11/2003 |
| WO | WO 2006/044394 A2 | 4/2006 |
| WO | WO 2006/108522 A1 | 10/2006 |

OTHER PUBLICATIONS

Wise et al, 2000. Handbook of Pharmaceutical Controlled Release Technology. Chapter 6. polylactic acid and polyglycolic acids as drug delivery carriers. Section IV.A. Copolymers with poly(ethylene glycol) and Poly(ethylene oxide). p. 119.*
Phoenix Chemical, 2002. Phoenix Chemical, Inc website PECOSIL—Silicone Organofunctionals. Available to the public on the web May 24, 2002; captured Jun. 1, 2009.*

* cited by examiner

*Primary Examiner*—Bennett Celsa
*Assistant Examiner*—Raymond P Yeager
(74) *Attorney, Agent, or Firm*—Ronald T. Sia; Kevin C. Johnson; Steven W. Miller

(57) ABSTRACT

Razors and components thereof are provided, as well as methods of making such.

5 Claims, 11 Drawing Sheets

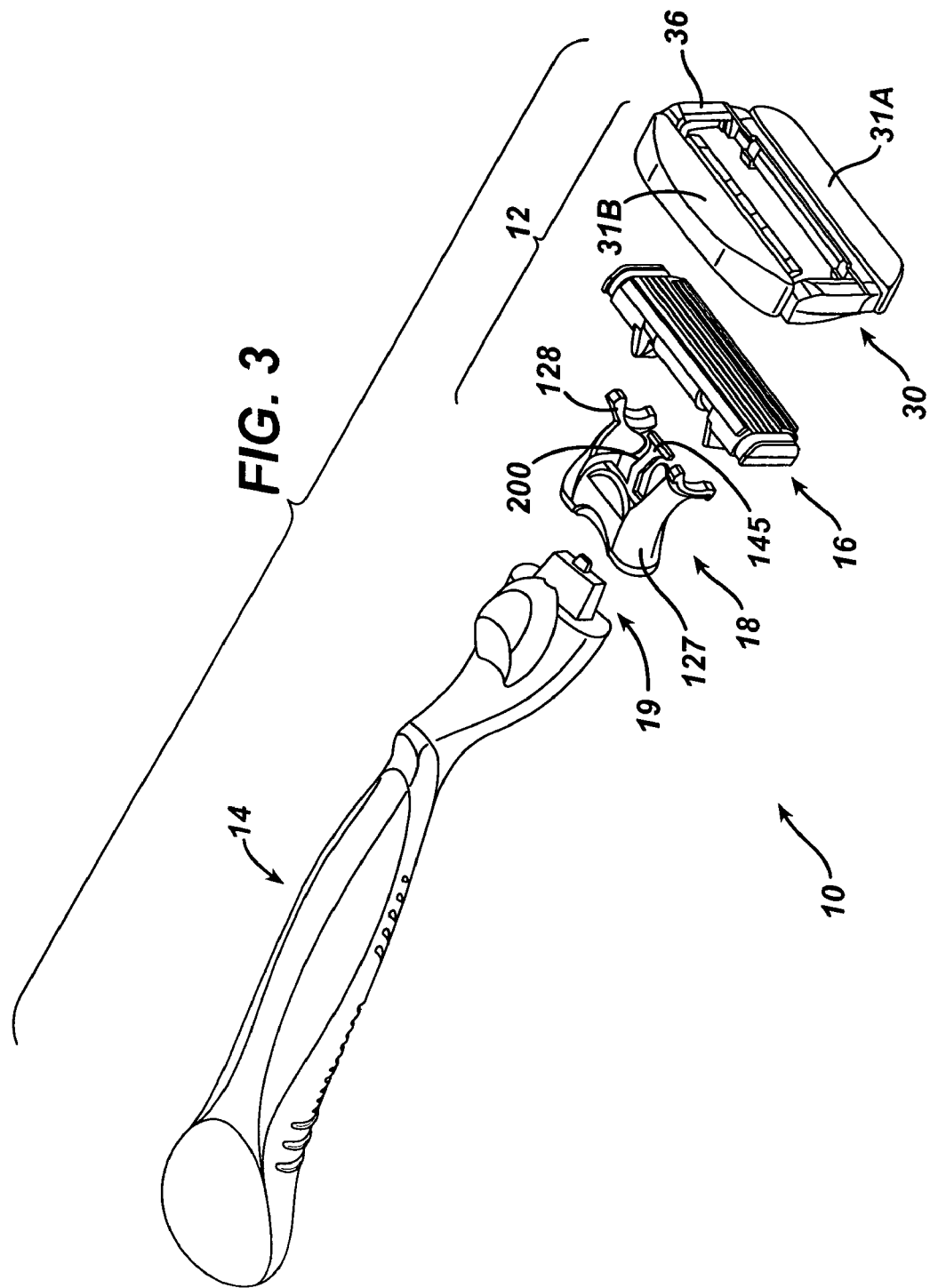

MOLDED SHAVING AID COMPOSITIONS, COMPONENTS AND METHODS OF MANUFACTURE

CROSS REFERENCE TO RELATED APPLICATIONS

This application claims the benefit of U.S. Provisional Application No. 60/735,758 filed Nov. 9, 2005 under 35 U.S.C. 120.

TECHNICAL FIELD

This invention relates to shaving preparations, razors, and cartridges.

BACKGROUND

Razors for wet shaving typically include a blade unit carried by a handle, the blade unit including one or more elongate blades, each with a sharpened edge (e.g., a rectilinear sharpened edge). The blade unit may be fixedly mounted on the handle with the intention that the entire razor be discarded when the blade edge or edges have become dulled. Alternatively, the blade unit can be detachably connected to the handle to enable replacement of a used blade unit with a fresh blade unit. Replaceable blade units are commonly referred to as cartridges.

Some shavers, in particular women, use this type of razor in the shower. For example, when shaving her legs a woman will often apply a film or lather of soap to an area of skin to be shaved, shave that area, apply soap to another area, and shave that area. This process is repeated until shaving is complete. Shaving in this manner may be difficult and frustrating, as it generally requires the shaver to hold a wet bar of soap in one hand while wielding a razor in the other hand, often while standing in an awkward position on a slippery shower floor.

Attempts have been made to address this problem by providing soap mounted on a razor. For example, U.S. Pat. No. 6,584,690 describes a razor that carries a shaving preparation, e.g., in the form of a solid cake of soap that surrounds the cartridge.

SUMMARY

Shaving aid compositions including a soap base and one or more wear enhancing ingredients are provided, as are methods of forming the shaving aid composition. The wear enhancing ingredients can increase the wear resistance of the shaving aid composition (as compared with a shaving aid composition lacking the wear enhancing ingredients), such that the compared with a shaving aid composition lacking the wear enhancing ingredients), such that the shaving aid composition lasts through a greater number of shaves and/or so that the shaving aid composition does not rapidly dissolve or disintegrate in the presence of water.

Many wear enhancing ingredients are process-sensitive. Many other desirable ingredients, for example, moisturizers, fragrances, and the like, may similarly be process-sensitive. Methods are provided that allow for the incorporation of such process-sensitive ingredients into a molded soap-based shaving aid composition. Generally, the shaving aid composition is formed by first making a melted soap base and incorporating the process-sensitive ingredients into the melted soap base to form a shaving aid composition. The shaving aid composition is subsequently cooled. The period of time elapsing between adding the process-sensitive ingredient and cooling the shaving aid composition is kept sufficiently short to prevent substantial degradation of the wear enhancing ingredient, for example, no more than about 1 hour. The resultant molded shaving aid composition can have greater wear resistance due to the presence of the wear enhancing ingredients. The molded shaving aid composition can be incorporated into a razor, for example, by incorporating it into a razor head or cartridge.

In a first aspect, shaving cartridges are provided that include a housing having a front edge and a rear edge, one or more shaving blades between the front edge and the rear edge, and a shaving aid holder. The cartridges include at least one shaving aid portion mounted on the shaving aid holder. The shaving aid portion includes from about 0.1 to about 10 wt % polyoxyethylene and a poured soap base.

In another aspect, razor components that are configured to attach to a razor are provided. The razor components include a molded shaving aid portion and a shaving aid holder to which the molded shaving aid portion is mounted. The molded shaving aid portion includes from about 0.1 to about 10 wt % polyoxyethylene and a soap base.

In another aspect, compositions are provided that include from about 0.1 to about 10 wt % polyoxyethylene and a poured soap base.

In a method aspect, methods of making a molded shaving aid portion are provided. The methods include heating a soap base to a temperature sufficient to melt the soap base, adding one or more process-sensitive ingredients to the soap base melt to form a shaving aid composition, and cooling the shaving aid composition to form a molded shaving aid portion. A period of time between adding the process-sensitive ingredient and cooling the shaving aid composition is kept sufficiently short to prevent substantial degradation of the wear enhancing ingredient.

Embodiments can include one or more of the following features.

The shaving aid composition can have from about 1 wt % to about 5 wt % polyoxyethylene. The polyoxyethylene can have a molecular weight of from about 100,000 to about 5,000,000. The shaving aid composition can further include a silicone polymer (e.g., from about 0.25 wt % to about 5 wt % silicone polymer). The shaving aid composition can further include a polyethylene, polybutene, and mineral oil composition. The composition can include from about 0.25 wt % to about 5 wt % silicone polymer, from about 10 wt % to about 60 wt % fatty acid salts, from about 0.1 wt % to about 8 wt % esters, from about 0.25 wt % to about 10 wt % polyoxyethylene, and from about 0.3 wt % to about 10 wt % of a polyethylene, polybutene and mineral oil composition. The soap base can be a poured soap base, an extruded soap base, or a combination thereof.

The process-sensitive ingredient can be a wear enhancing ingredient. The period of time elapsing between adding the process-sensitive ingredient and cooling the shaving aid composition can be, for example, no more than about 1 hour. The shaving aid composition can be poured into a mold prior to cooling. The method can further include saponifying tallow or vegetable fat to form the soap base. The method can further include forming the soap base by melting a first composition comprising a glycol and a fatty acid salts to form the soap base. The first composition can further including glycerine, a C15-C25 alcohol, stearic acid, microcrystalline wax, and surfactants (e.g., sodium lauryl ether sulfate). The shaving aid portion can be made in a continuous process. The molded shaving aid portion can be incorporated into a razor blade unit.

Process-sensitive ingredients are those ingredients that would be subject to degradation or partial degradation when exposed to the process conditions (e.g., temperatures, shear forces and time) involved in the formation of the soap base. These ingredients may be able to withstand process conditions for a shorter duration of time than is involved in forming the soap base, or may be able to withstand some of the process conditions (e.g., temperature or shear force) involved over the period of time involved in forming the soap base but not all of the process conditions over that duration of time and still be considered process sensitive.

Embodiments can include one or more of the following advantages.

The molded shaving aid composition can exhibit increased wear resistance and/or durability, as compared with a shaving aid composition that do not include wear-enhancing ingredients. The molded shaving aid composition can last through more shaves, can last longer when exposed to a moist environment and/or to water, and/or can provide other desirable shave attributes.

The molded shaving aid in some embodiments can be reduced in size while providing the same number of shaves as a shaving aid composition lacking the wear enhancing ingredients. This can permit the overall volume of the razor head to be reduced, which can improve performance and/or the aesthetic appearance of the razor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims. In the descriptions herein, all percentages are weight percentages, based on the weight of the overall shaving aid composition, unless otherwise indicated.

DESCRIPTION OF DRAWINGS

FIG. 3 is an exploded perspective view of the razor of FIG. 1.

Like reference symbols in the various drawings indicate like elements.

DETAILED DESCRIPTION

Figure 1A:
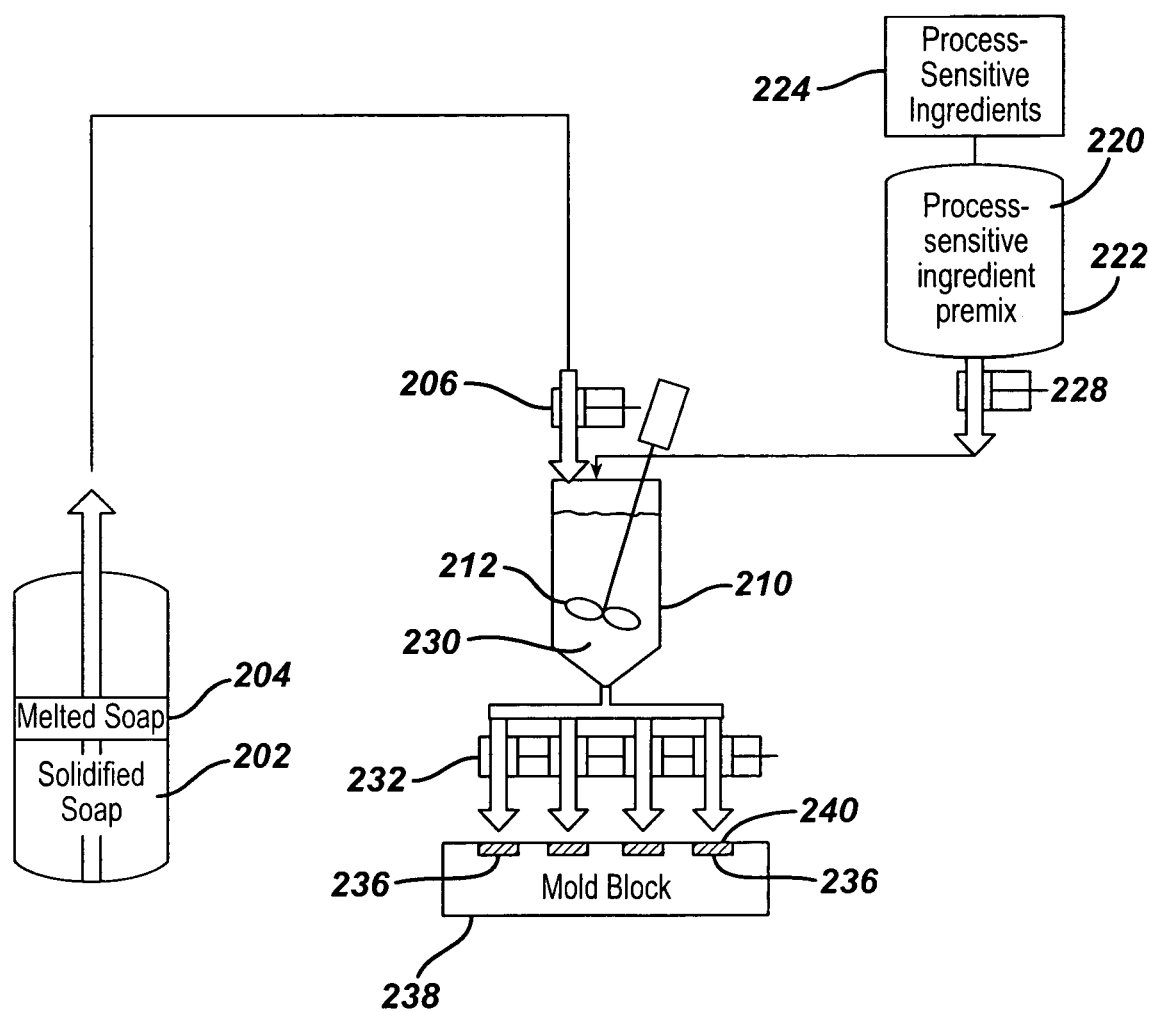
FIG. 1A is a diagram of a process of forming a molded shaving aid composition utilizing a poured soap base.

Razors having shaving aid compositions that are soap based can be used without the need for a separate shaving aid, such as, e.g., soap or shaving cream or gel, which can simplify razor usage, for example, by permitting shaving in the shower without the need for continued reapplication of the shaving aid to the skin. It is desirable to increase the wear resistance of the shaving aid, such that the shaving aid composition lasts through a greater number of shaves than it would absent the increase in wear resistance, and/or so that the shaving aid composition does not rapidly dissolve or disintegrate in the presence of water. However, many wear enhancing ingredients that could improve the wear characteristics of a molded shaving aid composition are process-sensitive, and might degrade when exposed to the temperature and shear forces and period of time involved in the formation of a soap. Many other desirable ingredients, for example, moisturizers, fragrances, and the like, are similarly process-sensitive.

The present invention allows for the incorporation of such process-sensitive ingredients into a molded soap-based shaving aid composition. Generally, the shaving aid composition is formed by first obtaining (e.g., making) a soap base, e.g., an extruded soap base or a poured soap base. The process-sensitive ingredients are incorporated into the soap base to form a shaving aid composition. Generally, if the soap base is a poured soap base, this is achieved by melting the poured soap base, adding the process-sensitive ingredients, and then cooling the resultant composition, for example, by placing into a mold and cooling the composition, within a period of time in which the process-sensitive ingredients remain substantially non-degraded, e.g., within about 1 hour. Where the soap base is an extruded soap base, the soap base and the process-sensitive ingredients are combined by milling, grinding, and/or other mixing techniques, refined, and extruded to form a molded shaving aid composition. Generally, a good quality shaving aid composition can be achieved by avoiding remelting of the process-sensitive ingredients.

The resultant molded shaving aid composition can have greater wear resistance due to the presence of the wear enhancing ingredients. The molded shaving aid composition can be incorporated into a razor for example, by incorporating it into a razor head or cartridge.

Soap Base

The shaving aid composition includes a soap base, e.g., a poured soap base or an extruded soap base. The basic component of the soap base can be a vegetable oil or tallow, saponified or neutralized to form the base, or can be a synthetic poured soap base. Super-fatted materials containing portions (e.g., greater than about 25 weight percent) of coconut acid or other fatty acids may also be used. In some embodiments, the shaving aid composition includes a base comprising a vegetable oil or a tallow or the like, or a combination of the foregoing materials, which is saponified or neutralized. The saponification or neutralization of the vegetable oil or tallow results in the production of glycerol and salts of fatty acids to form the base. The shaving aid composition can include about 50 wt % to about 100 wt % saponified or neutralized base (e.g., about 75 wt % to about 100 wt % saponified or neutralized base), which may be opaque, translucent, or transparent. Exemplary salts of fatty acids that may be produced include sodium carboxylate salts having up to about 22 carbon atoms.

The soap base can be a synthetic soap base. In certain embodiments, the synthetic soap base includes a glycol (e.g., dipropylene glycol, propylene glycol, tripropylene glycol, and/or methylpropane diol glycol), glycerin, fatty acid salts (e.g., sodium stearate and/or potassium stearate), C15-C25 alcohols (e.g., behenyl alcohol, stearyl alcohol, cetyl alcohol, and/or myristic alcohol), steareth (e.g., a steareth 21 such as, for example, Brij®-721), stearic acid, microcrystalline wax (e.g., microcrystalline wax SP 16, SP 19, SP 16, SP 18, SP-1674, SP 16W, SP 60W, SP 89, Multiwax 180M, X-145, W-445, and/or W-835), one or more surfactants (e.g., Tegobetaine F-50, Lonzaine®, the Mackam® family of surfactants, the Mirataine® family of surfactants, and sodium lauryl ether sulfate ("SLES") (e.g., 25% active SLES). In some embodiments, glycerin is not included in the soap base. Glycerin can optionally be included, in part or in whole, in a process sensitive phase described in greater detail below.

The soap base can, in certain embodiments, include from about 0.5% to about 30% glycol (e.g., from about 10% to about 25% glycol or from about 12% to about 15% glycol), from about 10% to about 40% glycerin (e.g., from about 18% to about 34% glycerin or from about 18% to about 24% glycerin), from about 20% to about 40% fatty acid salt (e.g., from about 25% to about 40% fatty acid salts (e.g., stearate) or from about 30% to about 35% fatty acid salt), from about 0.1% to about 10% stearic acid (e.g., from about 2 to about 5% stearic acid), from about 0.5% to about 10% microcrystalline wax (e.g., from about 0.5% to about 5% microcrystalline wax or from about 1% to about 3% microcrystalline wax), from about 1% to about 15% betaine (e.g., from about 2% to about 10% active betaine or from about 4% to about 9% active betaine), and from about 1 to about 20% active SLES (e.g., from about 1% to about 20% active SLES or from about 10% to about 15% active SLES), all based on the weight of the poured soap base. One exemplary poured soap base includes the following:

| | |
|---|---|
| Dipropylene glycol | 17.2% |
| Glycerin | 21.4% |
| Sodium stearate | 34.4% |
| Stearic acid (Pristerene ® 4980) | 3.7% |
| Microcrystalline wax SP 89 | 1.2% |
| Tegobetaine F-50 | 7.4% |
| SLES, 25% active | 14.7% |

In some embodiments, a combination of base and synthetic surfactants can also be employed.

Commercially available soap bases can be employed. Exemplary commercially available soap bases include, for example, clear translucent soap bases available from Twincraft Soap.

Wear Enhancers

The shaving aid composition includes one or more wear enhancing ingredients. Suitable wear enhancing ingredients include sodium stearate, polyoxyethylene, polyethylene, esters, and silicone polymers. Many of these ingredients (e.g., esters and polyoxyethylene) are typically process-sensitive. Wear enhancing materials can also impart other qualities or characteristics to the shaving aid composition, such as, e.g., increased lubrication.

Polyoxyethylene

One suitable wear enhancing ingredient is polyoxyethylene, which is a process-sensitive material. Polyoxyethylenes are typically characterized by their nominal, or average (number average), molecular weight. The number average molecular weight is the sum of individual molecular weights divided by the number of polymers. As is known in this field, a sample of polyoxyethylene generally includes a distribution of molecular weights such that the sample will include individual polymer molecules above and below the number average molecular weight.

Inclusion of a polyoxyethylene of any nominal molecular weight can improve the wear characteristics of the molded shaving aid composition. The polyoxyethylene can have an approximate nominal molecular weight of, for example, no less than about 100,000 daltons (e.g., no less than about 500,000, 1,000,000, 2,000,000, 3,000,000, 4,000,000, 5,000,000, 6,000,000, or no less than about 7,000,000 daltons) and/or no more than about 8,000,000 daltons (e.g., no more than about 7,000,000, 6,000,000, 5,000,000, 4,000,000, 3,000,000, 2,000,000, or no more than about 1,000,000 daltons). Optionally, two or more polyoxyethylenes having different nominal molecular weights can be employed. The polyoxyethylene can be present, for example, at a level of no less than about 0.1% (e.g., no less than about 0.25%, no less than about 0.5%, no less than about 1%, no less than about 2%, no less than about 3%, no less than about 4%, no less than about 5%, no less than about 6%, no less than about 7%, no less than about 8%, or no less than about 5%, no less than about 6%, no less than about 7%, no less than about 8%, or no less than about 9%) and/or no more than about 10% (e.g., no more than about 9%, no more than about 8%, no more than about 7%, no more than about 6%, no more than about 5%, no more than about 4%, no more than about 3%, no more than about 2%, no more than about 1%, or no more than about 0.5%), based on the weight of the shaving aid composition. Exemplary polyoxyethylenes include members of the POLYOX® family of polyoxyethylenes, available from Union Carbide Corporation, and ALKOX® polyoxyethylenes, available from Meisei Chemical Works, Kyoto, Japan.

Silicone Polymers

Silicone polymers can also be employed as a wear enhancing ingredient. In particular, silicone cross-polymers may be used. Silicone cross-polymers are polymers including silicone (e.g., having a silicone-based backbone) that are capable of cross-linking (e.g., that are cross-linked). Silicone polymers, particularly silicone cross-polymers, can be present at levels of at least about 0.25% active in a solvent (e.g., at least about 0.5%, 1%, 1.5%, 2%, 2.5%, 3%, 3.5%, 4%, or at least about 4.5%) and/or at most about 5% (e.g., at most about 4.5%, 4%, 3.5%, 3%, 2.5%, 2%, 1.5%, 1%, or at most about 0.5%). In certain embodiments, the silicone cross-polymer will be present at levels of from about 0.25% to about 5%. Exemplary silicone cross-polymers include, for example, lauryl dimethicone/polyglycerin-3 cross-polymer (e.g., 30% lauryl dimethicone/polyglycerin-3 cross-polymer).

Commercially available silicone cross-polymers include dimethicone PEG-7 panthenyl phosphate (Pecosil® PAN-400), dimethicone PEG-7 phosphate (Pecosil® PS-200), dimethicone PEG-7 undecylenate (Pecosil® DCU), dimethicone/methicone copolymer (Pecosil® SH-25L), and perfluoronoylethyl dimethicone methicone copolymer (Pecosil® FS-H15), each available from Phoenix Chemical, Inc.; dimethicone/vinyl dimethicone crosspolymer in dimethicone (KSG 16), vinyl dimethicone/lauryl dimethicone crosspolymer in mineral oil (KSG 41), vinyl dimethicone/lauryl dimethicone crosspolymer in squalane (KSG 44), vinyl dimethicone/methicone silsesquioxane crosspolymer (KSP-100, KSP-101, KSP 105), squalene and lauryl dimethicone/polyglycerin-3 crosspolymer (KSG 840), triethylhexanoin and lauryl dimethicone/polyglycerin-3 crosspolymer (KSG-830), and dimethicone/polyglycerin-3 crosspolymer and dimethicone (KSG-710), each available from Shin-Etsu; PEG/PPG-20/6 dimethicone (ABIL® B88184), behenoxydimethicone (ABIL® wax 2440), and C24-28 alkyl methicone (ABIL® wax 9810P), each available from Degussa; and dimethicone/vinyl dimethucine crosspolymer and C12-C14 Pareth-12 (DC9509), available from Dow Corning.

Esters

Esters (for example, butters and other non-liquid esters) can be incorporated into the shaving aid composition, and can function as a wear enhancer and/or as a skin-softener. In particular, semi-solid esters may be employed and they are generally process-sensitive materials. The semi-solid esters can act as an emollient and/or as a moisturizer. Exemplary semi-solid esters include butters such as, for example, shea butter, cocoa butter, kokum butter, avocado butter, olive butter, mango butter, and mixtures thereof. Esters can be incorporated into the shaving aid composition in levels of no less than about 0.5% (e.g., no less than about 1%, 2%, 3%, 4%, 5%, 6%, or no less than about 7%) and/or no more than about 8% (e.g., no more than about 7%, 6%, 5%, 4%, 3%, 2%, or no more than about 1%).

Polyethylene Compositions

The shaving aid composition can include one or more polyethylene compositions as wear enhancing ingredients. Generally, polyethylenes can improve the wear characteristics of the shaving aid composition, but are difficult to incorporate into the composition directly. Instead, the polyethylenes can be incorporated into a composition that is then incorporated into the shaving aid composition. For example, a composition including polyethylene, polybutene, and mineral oil (for example, sold under the trade name Covagloss by Sensient Technologies) can be employed. In some embodiments, the shaving aid composition will include no less than about 0.5% (e.g., no less than about 1%, 2%, 3%, 4%, 5%, 6%, or no less than about 7%) and/or no more than about 8% (e.g., no more than about 7%, 6%, 5%, 4%, 3%, 2%, or no more than about 1%) of a polyethylene, polybutene, and mineral oil composition.

Moisturizer Components and Other Optional Ingredients

The shaving aid composition can further include other skin care ingredients and/or other additives. Skin care ingredients that may be added to the base to enhance the composition include, but are not limited to, surfactants (e.g., sodium isostearoyl lactylate, ammonium isostearate, DEA-myristate, alkyl glyceryl sulfonate, and laureth-16), skin care agents (e.g., emollients, lubricants, humectants, moisturizing agents, and conditioners), foaming agents, hair growth inhibitors, botanical extracts, antioxidants, antimicrobials, anti-inflammatory agents, astringents, anti-irritants, depilatory agents, medicinal agents, absorbents, fragrances, coloring agents (e.g., dyes and pigments) and exfoliating agents (e.g., loofa, seaweed, oatmeal, pumice, apricot seed, and the like). Exemplary embodiments of skin care agents include, but are not limited to, humectants such as glycerin, sorbitol, and propylene glycol, skin freshening and soothing agents such as menthol, aloe, allantoin and collagen, lubricants such as polyoxyethylene, and silicones (e.g. dimethicone, dimethiconol, dimethicone copolyol, stearyl dimethicone, cetyl dimethicone copolyol, phenyl dimethicone, cyclomethicone, etc.), sodium or potassium salts (e.g., lactylates, chlorides, sulfonates, and the like), vitamins and vitamin complexes (including vitamin precursors and derivatives), cocoates, metal oxides, oils (e.g., cocoa butter), dimethicone, allantoin, sucrose cocoate, oleyl lanolate, thiourea, tocopheryl acetate, PPG-33, undeceth-3, honey, algae and aloe barbadensis. The skin care ingredients can in some embodiments be present in amount of no more than about 35% (e.g., no more than about 30%, 25%, 20%, 15%, 12%, 10%, 8%, 6%, 4%, or no more than about 2%). The absorbents can be clays or clay-based compositions, kaolin, wood powder, sodium chloride, cyclodextrin, chalks, talcs, silicas, polytetrafluoroethylene, or the like, and can be present in amounts of no more than about 9% (e.g., no more than about 5% or no more than about 3%). Clays that may be added include bentonite, kaolin, combinations of the foregoing clays, and the like.

Exemplary coloring agents include dyes and pigments, for example, titanium dioxide, manganese violet, zinc oxide, an Ultramarine (e.g., Ultramarine Blue 4), Orange 4, Green 3, or other dyes or pigments approved for use in cosmetics, either alone or in combination. Coloring agents can in certain embodiments be added in an amount of no more than about 6% (e.g., no more than about 4%, 2%, 1%, 0.1%, 0.01%, 0.001%, 0.0001%, or even no more than about 0.00001%) and/or no less than about 0.000001% (e.g., no less than about 0.00001%, 0.0001%, 0.001%, 0.01%, 0.1%, or no less than about 1%) by weight.

Fragrances are odorants used to impart desirable smells to the composition and may further mask the less desirable odors of other components of the composition. Any fragrance approved for use in cosmetics may be employed. In certain embodiments, at least one fragrance ingredient can be added in an amount up to about 4% (e.g., up to about 2%, up to about 1.5% or up to about 1%).

In certain embodiments, the molded shaving aid composition can be configured to provide an indication of wear to the user. For example, the molded shaving aid composition can include an indicia that appears or disappears as the shaving aid is exhausted. Such a wear indicator can indicate to the user when the razor cartridge should be replaced. In certain embodiments, the molded shaving aid compositions can be formulated and/or sized to be exhausted at the end of the intended life of the cartridge, so that running out of shaving aid will indicate to the user that the cartridge should be replaced. In other embodiments, the molded shaving aid compositions can include an embedded indicia, e.g., a logo or word, that appears when a predetermined amount of shaving aid has been washed away, or an indicia may be embossed on the shaving aid, which disappears as the shaving aid is used. In these cases, appearance or disappearance, respectively, of the indicia would indicate to the user that the cartridge should be replaced. Similarly, a lubricating strip may be mounted on one or both of the wings, underlying the molded shaving aid composition(s). In this case, as the shaving aid is exhausted the lubricating strip will be revealed, indicating that the cartridge should be replaced. The lubricating strip will provide the added benefit of lubrication and skin conditioning during the period of time until the user is able to replace the cartridge.

An exemplary process sensitive phase includes the following:

| | |
|---|---|
| Glycerin | 62.4% |
| Shea butter | 5.4% |
| Fragrance (IFF 4473-BH) | 5.4% |
| POLYOX ® WSR coagulant (MW approximately 5 million) | 26.9% |
| D&C Red 33 Dye | 0.005% |

Methods of Making the Molded Shaving Aid Composition

Two-step Process

1. Poured Soap Base

A poured soap base is formed, to which the process sensitive ingredients are subsequently added. The poured soap base can be a tallow or vegetable-based soap base, a synthetic soap base, or a combination of these. To prepare a fat-based soap base, tallow (fat from animals such as cattle and sheep) or vegetable fat is heated in the presence of a base, such as, for example, sodium hydroxide or potassium hydroxide. The fat/base mixture can be heated to between about 75° C. and about 100° C. Triglycerides in the tallow or vegetable fat react with the base to produce glycerol and a fatty acid salt (e.g., stearate or more particularly sodium stearate), or soap. Once this saponification reaction is complete, the soap is precipitated, for example, by adding a salt such as sodium chloride. Water and glycerol are then removed, for example, by vacuum distillation. The crude soap obtained from the saponification reaction can contain impurities, such as, for example, sodium chloride, sodium hydroxide, and residual glycerol. These impurities can be removed by boiling the crude soap curds in water and re-precipitating the soap with salt. This purification process can be repeated several times as needed.

In certain embodiments, a synthetic soap base is prepared. A synthetic poured soap base can be prepared by first blending or mixing the glycol and glycerin. The glycol/glycerine blend is heated to a first temperature sufficient to melt a fatty acid salt (e.g., at least about 90° C., at least about 95° C., at least about 100° C., or at least about 105° C.), and the fatty acid salt is added to the blend, which can be brought to a higher temperature to aid in incorporation of the fatty acid salt (e.g., at least about 85° C., at least about 90° C., at least about 95° C., at least about 100° C., at least about 105° C., or at least about 110° C.). The stearic acid and the microcrystalline wax are then added to the melt. The betaine and sodium lauryl ether sulfate are then added to the melt (as are the optional alcohol and steareth, if such are employed), and additional fatty acid salt is then added to the melt. The melt is cooled and allowed to solidify. The melt can optionally be allowed to solidify in any form, for example, in molds, bars, flakes, ribbons, pastilles, prills, or any other form. The solidified soap base can then be further processed, or can be stored (e.g., for as much as 2 years).

In certain embodiments, the process of forming the soap base includes elevating the soap base ingredients to a temperature of no less than about 80° C. (e.g., no less than about 85° C., 90° C., 95° C., 100° C., or 105° C.). The soap base ingredients are in some embodiments subjected to these temperatures for a period of time no less than about 1 hour (e.g., no less than about 2, 3, 4, 5, 10, or no less than about 20 hours).

2. Process-Sensitive Phase

A second phase is prepared, which can include one or more of the ingredients that are process-sensitive. The process-sensitive phase typically includes the esters, the polyoxyethylene, fragrances, dyes, and other optional ingredients. The process-sensitive phase can be prepared by warming glycerin to a temperature of from about 25° C. to about 50° C. (e.g., to about 35° C.) and adding the process-sensitive ingredients. The elevated temperature can aid in the incorporation of the process sensitive ingredients, and can be selected on the basis of the particular ingredients that are being incorporated. For example, butters typically melt at about 35° C., so raising the temperature of the process-sensitive phase to about 35° C. can aid in melting the butters into the phase. The selection of ingredients and amounts of the ingredients selected will vary, depending on the levels desired in the final shaving aid composition. In some embodiments, ingredients that are not themselves process-sensitive can be included in the process-sensitive phase.

The temperature of the process-sensitive phase can in certain embodiments be maintained at from about 25° C. to about 50° C. (e.g., at about 35°) until such time as the process-sensitive phase is added to the soap base. In other embodiments, the process-sensitive phase can be allowed to cool (e.g., to room temperature) prior to being incorporated into the soap base.

3. Combining the Soap Phase and the Process-Sensitive Phase

An embodiment of the formation of the shaving aid composition from a soap phase and a process-sensitive phase is illustrated in FIG. 1. A solidified poured soap base 202 is heated to a temperature of from about 90° C. to about 100° C. (e.g., to about 91° C., about 92° C., about 93° C., about 94° C., about 95° C., about 96° C., about 97° C., about 98° C., about 99° C., or about 100° C.) and remelted to form a melted soap 204. The melted soap 204 is metered via a pump 206 into a heated filler feed vessel 210 that is equipped with a stirring mechanism 212. Filler feed vessel 210 is configured to maintain the temperature of its contents at about 95° C. A process-sensitive phase 220 is formed by intermixing the process-sensitive ingredients 224 in heated chamber 222. The process-sensitive phase 220 is then metered via pump 228 into the filler feed vessel 210 and intermixed with the soap base 202 to form a molten shaving aid composition 230. Mixing is in some embodiments required to obtain a homogeneous end product; mixing is in general kept to a minimum to reduce shear forces that might degrade some or all of the process-sensitive ingredients. In other embodiments, a non-homogeneous blend can be utilized. For example, the desired end product can include one or more ingredients distributed in a pearlized, striated, or other non-homogeneous fashion in the soap.

The molten shaving aid composition 230 is then metered via fill pumps 232 into individual molds 236 formed in a mold block 238, where the shaving aid composition is cooled to form molded shaving aid compositions 240. The temperature of the molten shaving aid composition 230 is maintained at a temperature of about 95° C. until the shaving aid composition is placed in the molds 236.

Because the molten shaving aid composition 230 includes process-sensitive ingredients 224, the molten shaving aid composition 230 is held at the elevated temperature for a period of time that is less than would result in substantial degradation of the process-sensitive ingredients 230. For example, in some embodiments, the molten shaving aid composition 230 is held at an elevated temperature for no more than about 120 minutes (including e.g., no more than about 110 minutes, no more than about 100 minutes, no more than about 90 minutes, no more than about 75 minutes, no more than about 60 minutes, no more than about 50 minutes, no more than about 40 minutes, no more than about 30 minutes, no more than about 20 minutes, no more than about 10 minutes, no more than about 5 minutes, or even no more than about 2 minutes) before it is placed into molds and cooled. In this fashion, a molded shaving aid composition can be formed in which the process sensitive ingredients are substantially non-degraded.

In certain embodiments, the shaving aid composition is placed into a mold having a shaving aid mounting device (e.g., the wings described below) already positioned in the mold. In this fashion, the shaving aid composition can embed itself into the shaving aid mounting device upon solidifying.

Once the shaving aid composition has cooled to a sufficient point (e.g., to the point that it has solidified enough to be easily separated from the mold), the shaving aid composition can be removed from the mold. In some embodiments, the shaving aid composition is allowed to cool to approximately room temperature before being removed from the mold. In other embodiments, the shaving aid composition is allowed to cool to a temperature no greater than about 80° C. (e.g., no greater than about 75° C., 70° C., 65° C., 60° C., 50° C., 40° C., no greater than about 30° C., no greater than about 25° C., no greater than about 20° C., no greater than about 15° C., no greater than about 10° C., no greater than about 5° C., or no greater than about 0° C.) before being removed from the mold.

One-Step Batch Process

In some embodiments, the process-sensitive ingredients can be added directly to the poured soap base melt in a one-step batch process. In one such embodiment, the poured soap base melt is maintained at about 95° C., and the process-sensitive phase is added to the melt to form the shaving aid composition without first cooling and then re-melting the poured soap base melt. The shaving aid composition is then placed into one or more molds and cooled. In another such embodiment, the process sensitive ingredients are mixed directly into the poured soap base melt without first being incorporated into a process sensitive phase. The resulting shaving aid composition is then placed into one or more molds and cooled. In each case, the composition is placed in molds and allowed to cool before enough time has elapsed to substantially degrade some or all of the process sensitive ingredients. In particular, the time that elapses between adding the process-sensitive ingredients to the melted soap base and placing the molten shaving aid composition into the molds and cooling the shaving aid composition should be less than an amount of time in which some or all of the process-sensitive ingredients typically would begin to degrade at the elevated temperature and shear of the intermixing step. Generally, this time will be less than about 90 minutes (e.g., less than about 80, 70, 60, 50, 40, 30, 20, 10, or less than about 5 minutes).

Continuous Process

In some embodiments, the molded shaving aid composition is prepared in a continuous process. The ingredients for the soap base are first combined and flowed through a heated chamber to increase the temperature of the ingredients to at least about 90° C. (e.g., at least about 95° C., 100° C., 105° C., 110° C., 115° C., or at least about 120° C.). The heated chamber and pumping mechanism are configured to permit a sufficient dwell time of the soap base components at the elevated temperature to allow for sufficient melting and intermixing of the ingredients.

Next, the melt is moved into a second chamber maintained at no more than about 100° C. (e.g., no more than about 90° C., no more than about 80° C., or no more than about 70° C.). In the alternative, the melt can be retained in the first chamber, and the temperature of the first chamber can be reduced to no more than about 100° C. (e.g., no more than about 90° C., no more than about 80° C., or no more than about 70° C.). While maintaining this temperature, the process-sensitive ingredients are introduced and mixed into the soap base melt to form the shaving aid composition. The ingredients can be introduced individually, or can be introduced in the form of process sensitive phase, which is described above. The shaving aid composition is then flowed into a mold, e.g., by injection molding, and cooled to form a molded shaving aid composition.

Extruded Soap

Figure 1B:
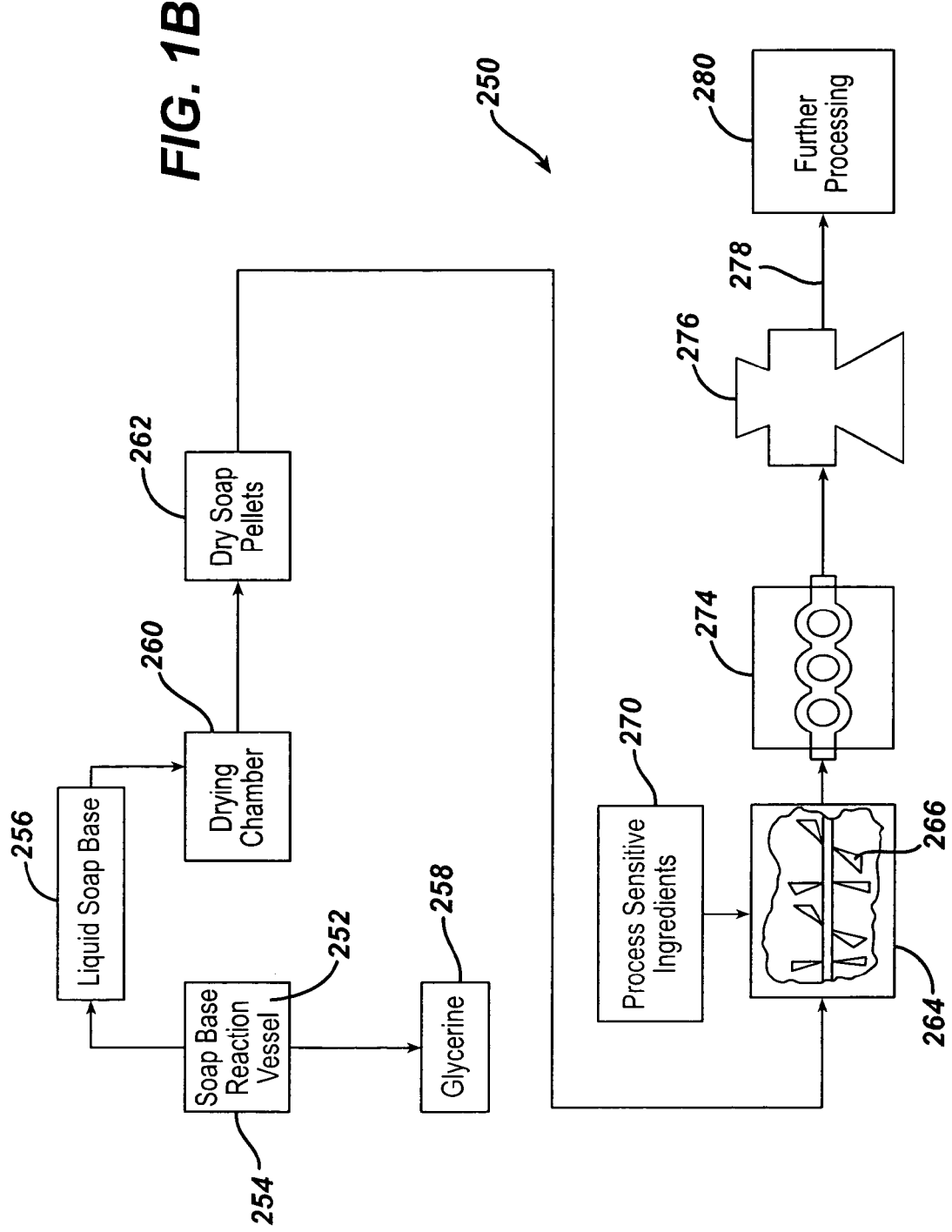
FIG. 1B is a diagram of a process of forming a molded shaving aid composition utilizing an extruded soap base.

An extruded soap can be employed in certain embodiments. A process 250 for forming an extruded soap is illustrated in FIG. 1B. The soap base is generally formed by combining the soap base ingredients 252 in a reaction vessel 254 to form a liquid soap base 256 (e.g., by saponification or neutralization reaction) and glycerine 258, which is removed from the liquid soap base 256. The liquid soap base is moved to a drying chamber 260 where at least some of the water is removed (e.g., by vacuum spray drying) to form substantially dry soap pellets 262 (e.g., dry soap noodles or shavings). The dry soap pellets 262 are then introduced into an amalgamator 264 having one or more paddles 266 for mixing and/or grinding the dry soap pellets 266 along with process sensitive ingredients 270, which are introduced into the amalgamator 264, to form an extruded soap dry blend 272. The extruded soap dry blend 272 can in some embodiments be macromolecularly homogenized (e.g., a substantially even distribution of the process-sensitive ingredients among the dry soap pellets can be achieved). The extruded soap dry blend 272 is then refined, e.g., by introducing the extruded soap dry blend 272 into one or more rolling mills 274 to achieve a substantially uniform texture. The extruded soap dry blend 272 is then extruded using an extruder 276, optionally using heat (e.g., not more than 95° C., 90° C., 85° C., 80° C., 70° C., 60° C., 50° C., 40° C., 30° C., or not more than 25° C.) and/or pressure, to form a continuous bar of extruded soap 278, which can be subjected to further processing steps 278 (e.g., cutting and/or stamping into the desired final shape).

Wear Characteristics of the Soap

In some embodiments, the shaving aid composition exhibits good wear characteristics. Wear characteristics can be determined in a number of ways. For example, the shaving aid composition can be incorporated onto a razor, and the number of shaves before certain shaving performance characteristics begin to degrade can be determined. In other embodiments, the wear can be determined by subjecting the shaving aid composition to set abrasive conditions (e.g., a given surface composition and speed of an abrasive device such as, e.g., an abrasive wheel) and determining how much of the composition wears off in a given time period.

In some embodiments, wear resistance can be measured by maintaining a flow of water over a textured surface and between this textured surface and the shaving aid body. The water is maintained in a water bath at a pre-selected temperature. The shaving aid body is abraded to simulate a shaving process. The flow of water through the water bath is about 0.08 gallons per minute (gpm), and the temperature of the water is from about 36° C. to about 40° C. Abrading of the shaving aid body is effected by an apparatus that provides for the engagement of the shaving aid body by a textured surface and for movement of the shaving aid body across the textured surface in an oscillating motion. The textured surface can be a stainless steel pad having a surface finish number of 32 microinches (Ra) (about 150 grit). Each continuous movement (forward and back) of the shaving aid body over the textured surface is a cycle. One complete cycle is a movement of about six inches in each direction (forward and back). A load of 300 grams (g) can be maintained on the shaving aid body 12 using weights. The % wear is determined by weighing the shaving aid body before beginning the test, weighing the shaving aid body after conclusion of the test (after running the test for a predetermined number of cycles, e.g., 30 cycles), and determining the percentage of shaving aid material that remains.

Another wear test utilizes cartridges of shaving aid composition molded to a holder and testing the cartridge using a wet wheel apparatus. The wet wheel apparatus has a rotating cylindrical wheel, e.g., having a diameter of about 10 inches, with the outer surface coated with an abrasive material (e.g., sandpaper, felt, or the loop portion of a hook-and-loop system such as a Velcro® system). The lower portion of the wheel dips into a water bath. A razor cartridge (without blades) is mounted in a holder located above the wheel so that the cartridge is held against the surface of the wheel with the aid of a standard pre-selected force (e.g., 200 g) as the wheel is rotated at a standard pre-selected rpm (e.g., 30 rpm). The temperature of the water bath in which the wheel circulates can be maintained at a given temperature, which can be from about 15° C. to about 45° C. The cartridge can be tested for a single duration of time (e.g., 3 minutes), or, to simulate multiple shaves over consecutive days, can be tested for a given duration of time (e.g., 1.5 minutes) over several days, allowing the cartridge to dry between test periods. In another method, the wheel is rotated a set number of rotations (e.g., 10, 20, 30, 40 or 50 rotations). The shaving aid composition is weighed prior to testing, and after testing is allowed to dry and equilibrate to room temperature (e.g., for a period of about 24 hours) and is reweighed.

Razors Including a Molded Shaving Aid Composition

Figure 2A:
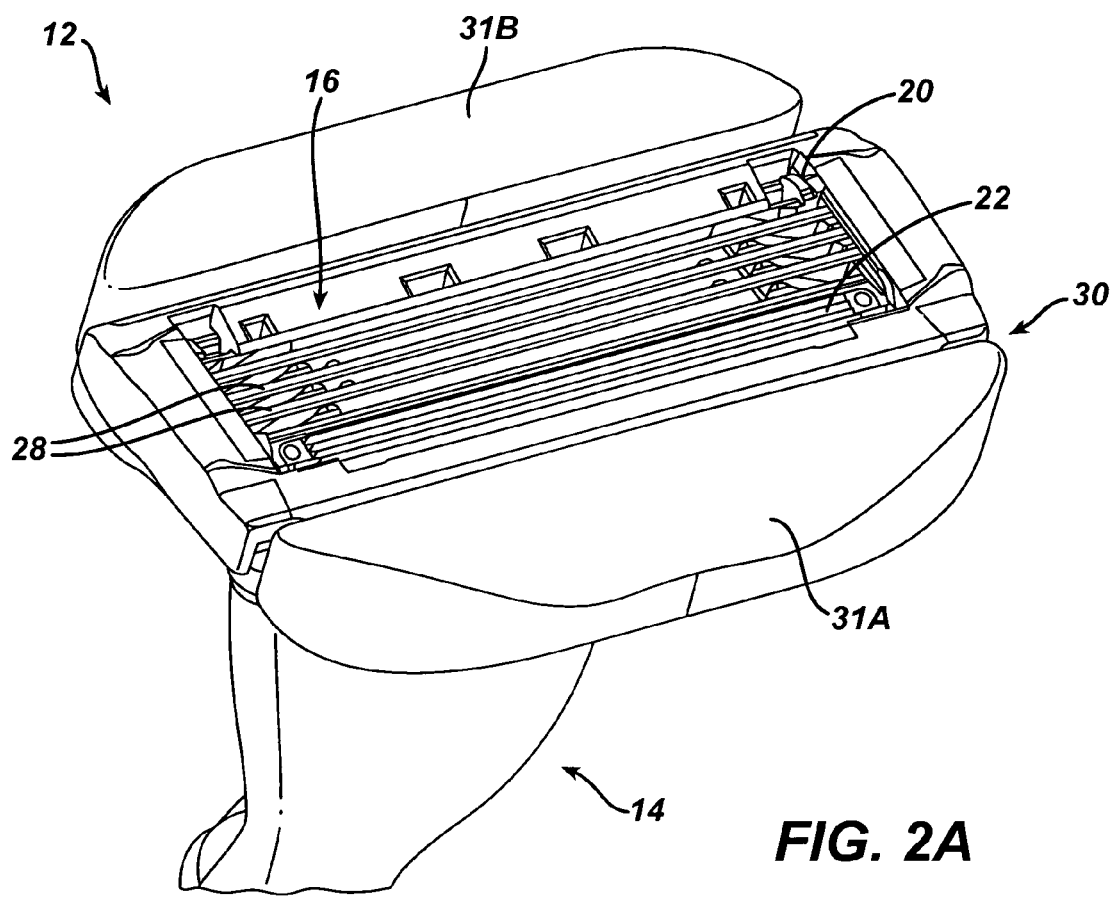
FIG. 2A is a perspective view of the head and neck portion of a razor according to one embodiment of the invention.
Figure 2B:
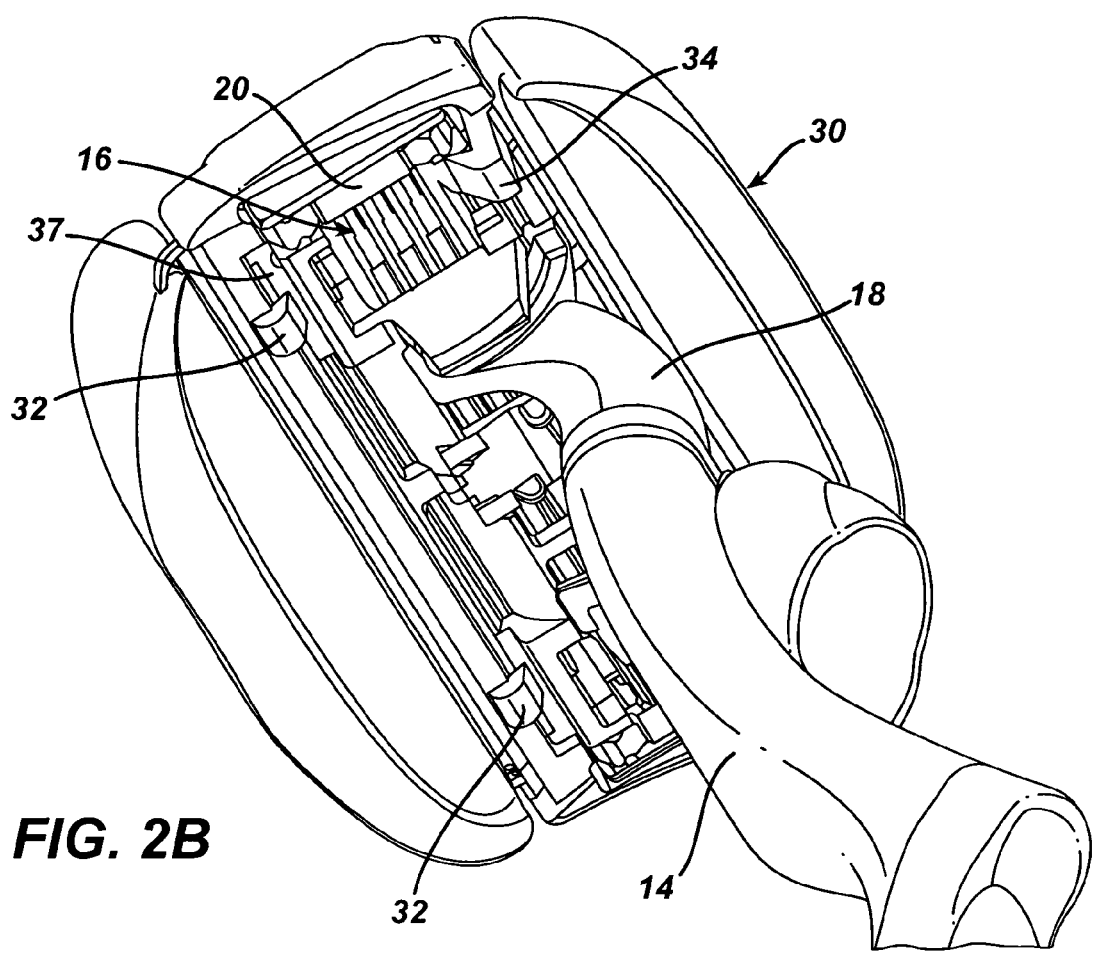
FIG. 2B is a perspective view of the head and neck portion shown in FIG. 1, viewed from the back.

The molded shaving aid compositions are in certain embodiments incorporated into a razor, e.g., into a razor head. For example, the molded shaving aid composition can be attached to one or more holders, which are themselves configured to be attachable to a razor head. Referring to FIGS. 2A, 2B, and 3, a shaving razor 10 includes a disposable cartridge 12 and a handle 14. As shown in FIG. 3, cartridge 12 includes a connecting member 18, which removably connects cartridge 12 to a connecting portion 19 of handle 14, a blade unit 16, which is pivotally connected to connecting member 18, and a shaving aid holder 30 mounted on the blade unit 16. Referring to FIG. 2A, the blade unit 16 includes a plastic housing 20, a guard 22 at the front of housing 20, and blades 28 between guard 22 and the rear of housing 20.

The blade unit 16 can be similar to blade units described in U.S. Pat. No. 5,661,907. The handle 14 can be similar to those described in U.S. Pat. Nos. 5,855,071, 5,956,851 and/or 6,052,903. The connecting member 18 that is used to connect blade unit 16 to handle 14 can be similar to connecting members described in U.S. application Ser. No. 10/969,373, titled "Shaving Razors and Cartridges," filed on Oct. 10, 2004, and U.S. application Ser. No. 10/969,392, titled "Shaving Razors and Cartridges," filed on Oct. 20, 2004.

As will be discussed in further detail below, the holder 30 carries a pair of shaving aid portions 31A, 31B. The front shaving aid portion 31A contacts the skin in front of the blades, i.e., before shaving, and the rear shaving aid portion 31B contacts the skin behind the blades. One or both of the shaving aid portions are formed of the molded shaving aid composition described herein, while one of the shaving aid portions can optionally include a different or additional composition. For example the front shaving aid portion may include the molded shaving aid composition, while the rear portion may include skin soothing and conditioning ingredients such as emollients and moisturizers in place of or in addition to the shaving aid portion.

Figure 4A:
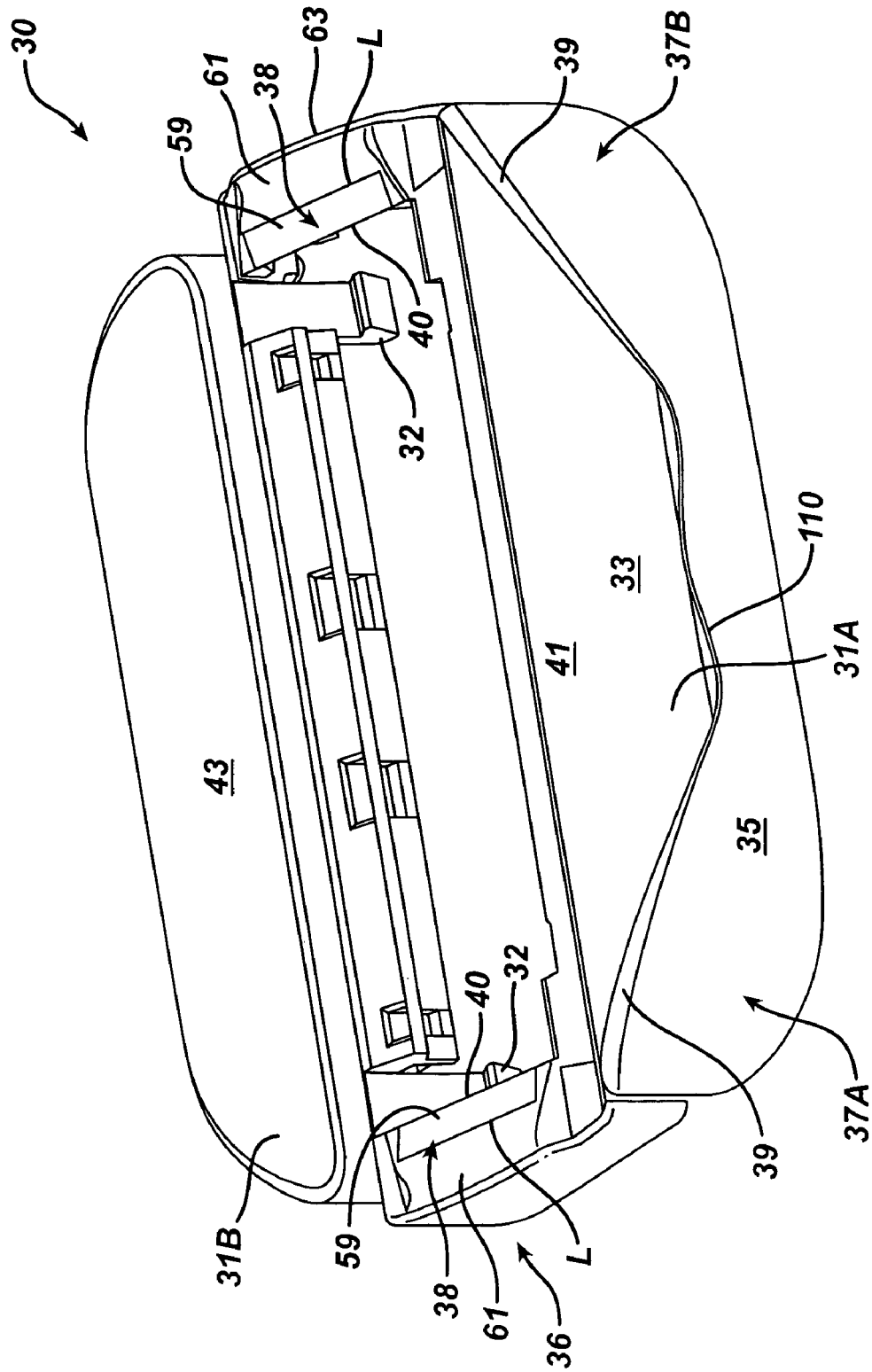
FIG. 4A is a perspective view of the holder portion of the cartridge shown in FIG. 1, viewed from above.
Figure 4B:
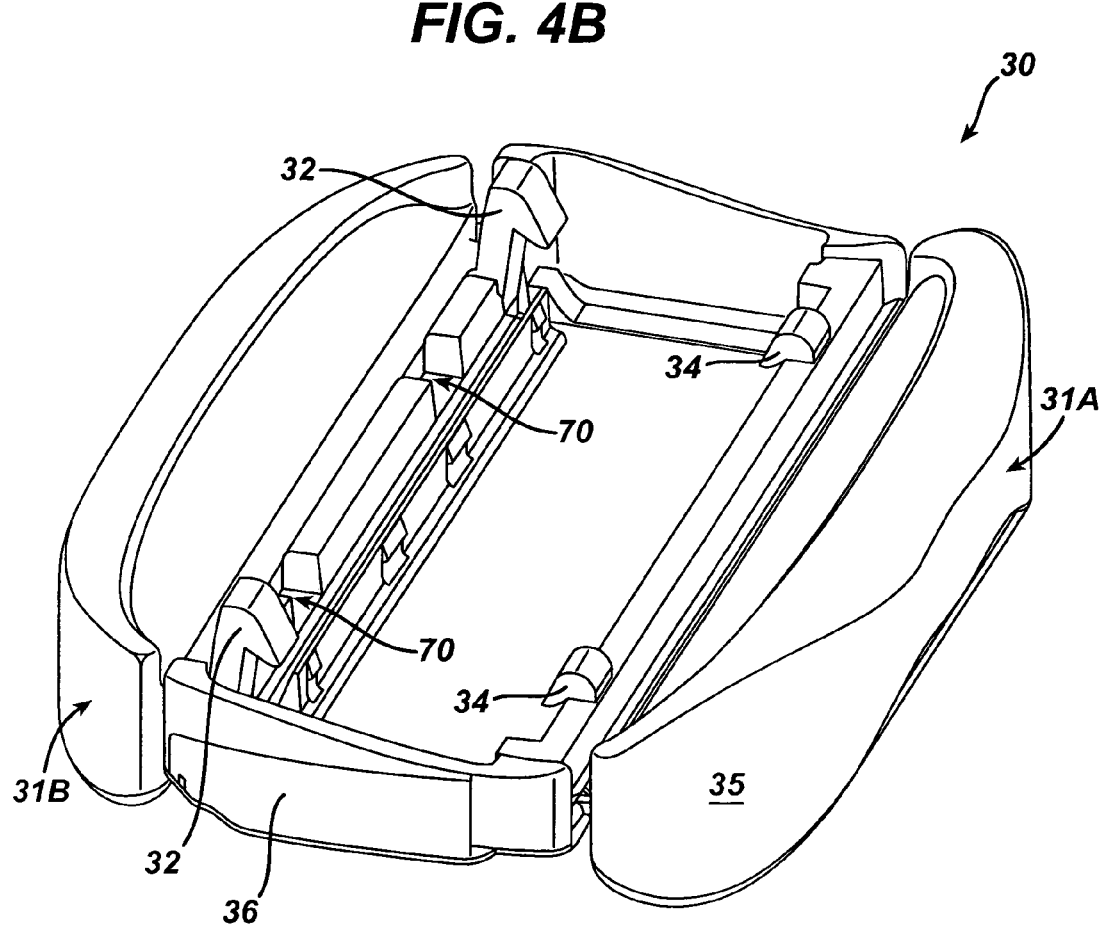
FIG. 4B is a perspective view of the holder shown in FIG. 3, viewed from below.
Figure 4C:
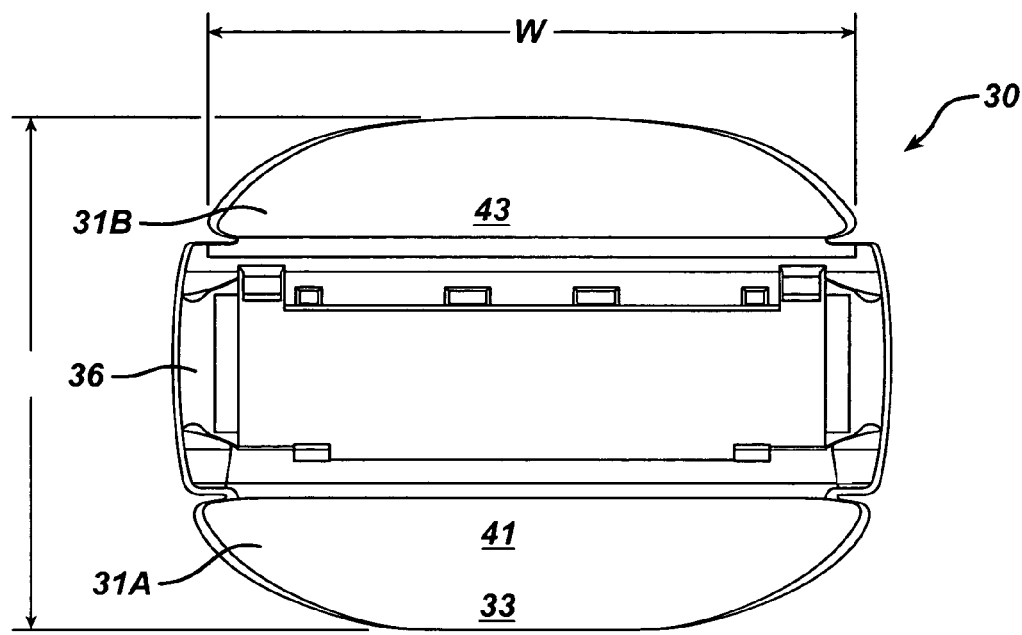
FIGS. 4C, 4D and 4E are, respectively, top, front, and side views of the holder shown in FIG. 3.
Figure 4D:
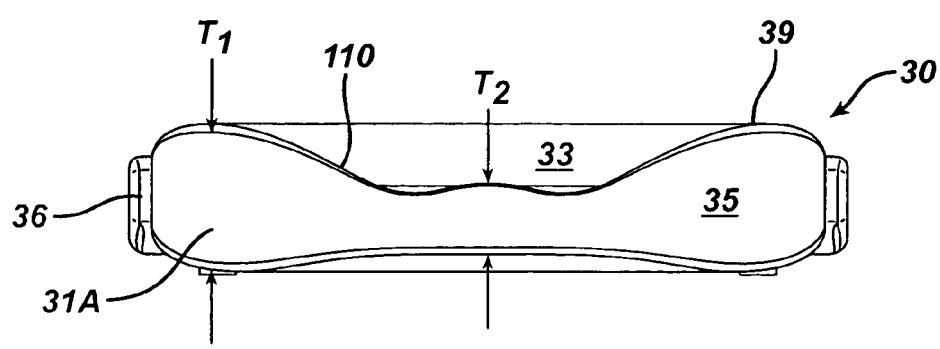
Figure 4E:
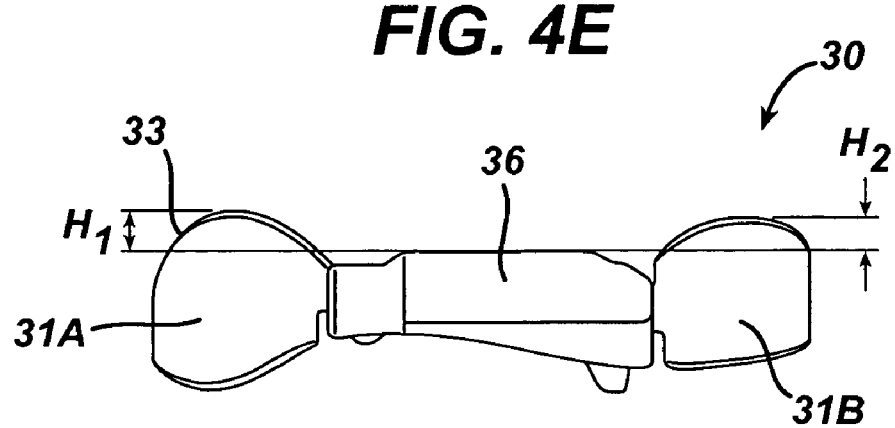
Figure 4F:
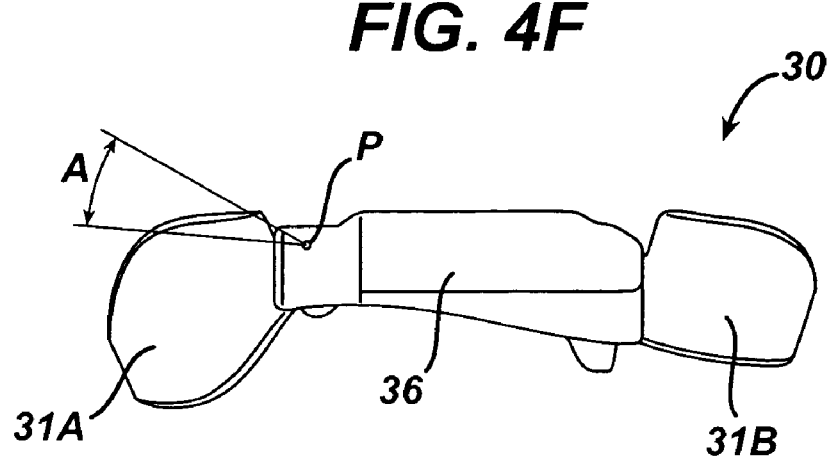
FIG. 4F is a side view showing the wings of the holder in a deflected position (the side mounts are shown in their normal position in FIG. 3D).
Figure 5A:
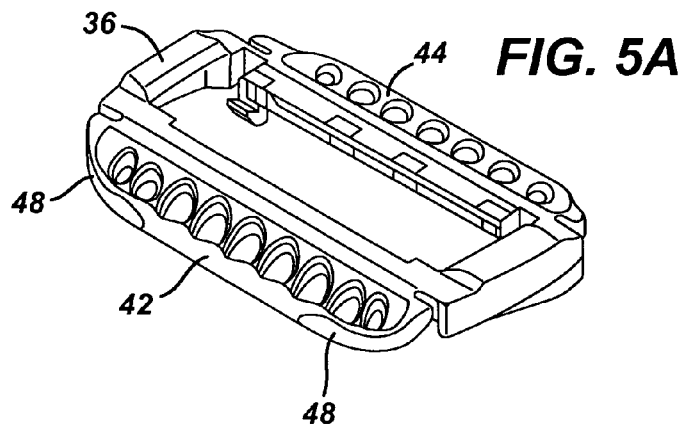
FIGS. 5A, 5B, 5C, and 5D are, respectively, perspective, top, front and side views of the holder with the shaving aid portions removed.
Figure 5B:
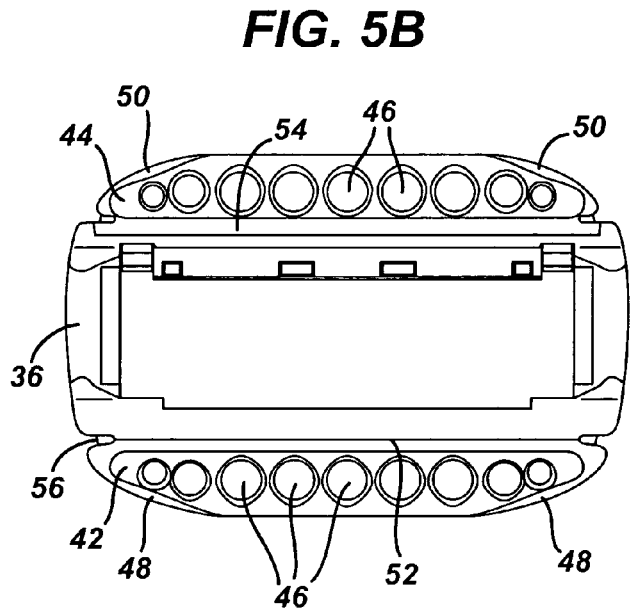
Figure 5D:
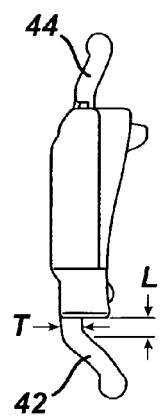
Figure 5C:
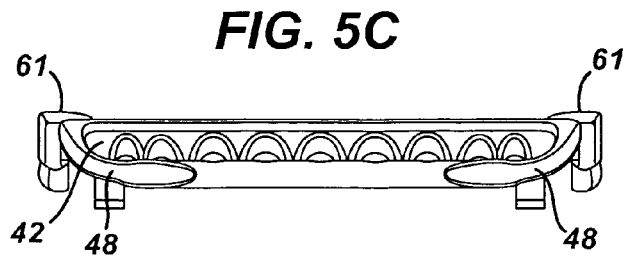

The shaving aid portions are mounted so that they will resiliently deflect upon contact with the skin, from a normal, undeflected position (FIG. 4E) to a flexed position (FIG. 4F). This deflection allows the razor to be easily used in hard to reach or confined areas, such as the armpit (axilla) or behind the knee. Deflection of the shaving aid portion also prevents premature wear of the shaving aid portion and discomfort to the user in cases where the user applies excessive pressure during shaving. Preferably, the angle of deflection (angle A, FIG. 4F) is at least about 10 degrees, e.g., from about 10 to 60 degrees, typically about 20 to 40 degrees. Angle A is measured by drawing a line from a pivot point P located in the approximate center of the elastomeric hinge to the highest point on the shaving aid portion 31A when the shaving aid portion is in its undeflected position, and measuring the angle between this line when the shaving aid portion is in its undeflected position and the same line when the shaving aid portion is deflected to its design limit. The resilient mounting of the shaving aid portions will be discussed in further detail below. The heights H1 and H2 of the shaving aid portions in the undeflected position (FIG. 4E) will vary, but may be, for example, from about 1 to 4 mm, e.g., about 1.5 to 3.0 mm. H1 and H2 are generally within about 0 to 50% of each other. Generally, the heights of the two shaving aid portions will be proportional to the wear rates of the compositions used, so that the shaving aid portions will be exhausted at approximately the same time.

The holder 30 may be mounted so that it is removable from the cartridge body by the consumer e.g., if the consumer wishes to add a shaving aid holder to a cartridge that does not include one), or, alternatively, may be permanently mounted on the cartridge body or integrally molded with the cartridge body. In the embodiment shown in FIGS. 2A-6D, the holder, 30 clips onto the cartridge by engagement of clips 32 and 34 (FIG. 4B) with the back surface 37 of the housing 20 of the blade unit, as shown in FIG. 2B. The holder 30 may be engaged with the housing by sliding the housing under clips 34 and then deflecting clips 32 to snap them in place.

Structure of the Shaving Aid Holder

Referring to FIG. 4A, shaving aid holder 30 includes a frame member 36 that extends around the periphery of the cartridge body when the holder 30 is in place. Generally, frame member 36 is formed of a molded plastic. In some embodiments, the sides 38 of the frame member extend over side regions of the cartridge body, to securely hold the holder in place. Sides 38 should generally be sufficiently thin, adjacent the blade ends, so that shaving performance is not compromised. In some embodiments, a ramped area is provided between the very thin edges 40 adjacent the blade ends to an area outboard of the edges. For example, the sides 38 generally have a thickness of less than 0.15 mm at edges 40, and less than 0.4 mm at line L, about 0.5 mm inboard of edges 40. This ramped area 59 provides rails 61, between line L and the outer side edge 63 of the holder 30, that may enhance tracking of the razor during use.

Referring to FIGS. 4E, 5A-5D and 6A-6D, shaving aid portions 31A and 31B are carried on a pair of wings 42, 44. Wings 42, 44 may be formed of the same plastic as the frame, or may be formed of a different material. For example, the wings may be formed of the same material as the hinges 52, 54 (FIG. 5B, discussed below) that join the wings and frame. In this case, the wings and hinges may be overmolded onto the frame in a single molding step.

The wings include a plurality of apertures 46 (FIG. 5B) that allow the shaving aid to flow through the thickness of the wing and form a mechanical interlock (e.g., by flowing together to form a unitary mass) on the back side of the wing, securing the shaving aid to the wing.

Elastomeric bumpers 48, 50 are provided at the corners of the wings, underlying the shaving aid portions, so that as the shaving aid portions are exhausted the user's skin will contact elastomer rather than hard plastic. Generally, the elastomeric bumpers have a thickness T (FIG. 6C) of at least 1 mm, e.g., about 1.5 to 3 mm. In some embodiments, the elastomer is relatively soft for user comfort and so that the hinge will have a soft flex. For example, the elastomer may have a hardness of less than about 50 Shore A, e.g., less than about 40 Shore A. The elastomer may be, for example, a block copolymer such as those available under the tradename KRATON®. In some embodiments, the elastomer has sufficient chemical resistance so that it will not degrade during prolonged contact with the ingredients of the shaving aid composition.

Figure 6D:
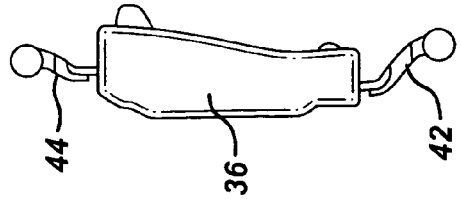
FIGS. 6A, 6B, 6C, and 6D are, respectively, perspective, top, front and side views of the holder with the shaving aid portions and elastomeric portions removed.
Figure 6A:
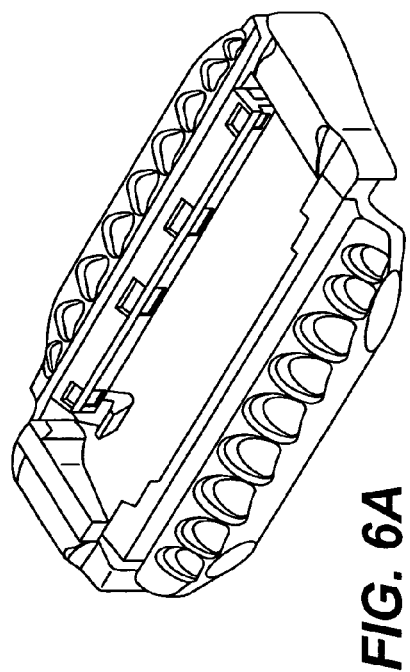

Referring to FIG. 6D, even in their normal, undeflected position, the wings 42, 44 curve downward, well below the plane defined by the blade edges. This curvature allows the wings to carry a relatively large amount of soap, without the upper surface of the shaving aid portion extending too far above the plane of the blade edges or the lowest area of the shaving aid portion being too low to ever contact the skin during use. Generally, the lowest point on each of the wings 42, 44 is at least about 1 mm below the plane defined by the blade edges, e.g., about 2 to 6 mm below this plane. If desired, e.g., if the shaving aid is relatively wear resistant, the wings may extend relatively straight from the frame.

Resilient Mounting of Shaving Aid Portions

Wings 42, 44 are resiliently mounted on the frame member 36, to allow deflection of the shaving aid portions 31A, 31B during shaving, from the normal position shown in FIG. 4E to the deflected position shown in FIG. 4F. Flexible hinges 52, 54 (FIG. 5B) provide this resilient connection between the wings and the frame.

In some embodiments, hinges 52, 54 are formed of an elastomeric material, e.g., a block copolymer. Typically, the hinges are formed of the same elastomeric material as the elastomeric bumpers 48, 50 discussed above. The elastomeric material is generally selected to provide a soft flex, so that the wings deflect readily upon contact with the user's skin, while also providing a good spring return to the wings. For example, the elastomeric material may have a flexural modulus of about 100 to 300 psi. The modulus that will provide the desired product characteristics will depend upon the thickness T and length L (FIG. 5D) of the hinges. The thickness and length of the two hinges can be the same or different, and these dimensions and the elastomeric material used can be selected to give the two wings desired flexural characteristics. The thickness of the hinges may be, for example, from about 0.5 to 2.0 mm and the length may be from about 0.5 to 3.0 mm. In the embodiment shown in FIGS. 5A-5D, the hinges extend almost the full width of the holder 30. However, if desired, the hinges may be narrower or may consist of discontinuous hinge portions.

Figure 6B:
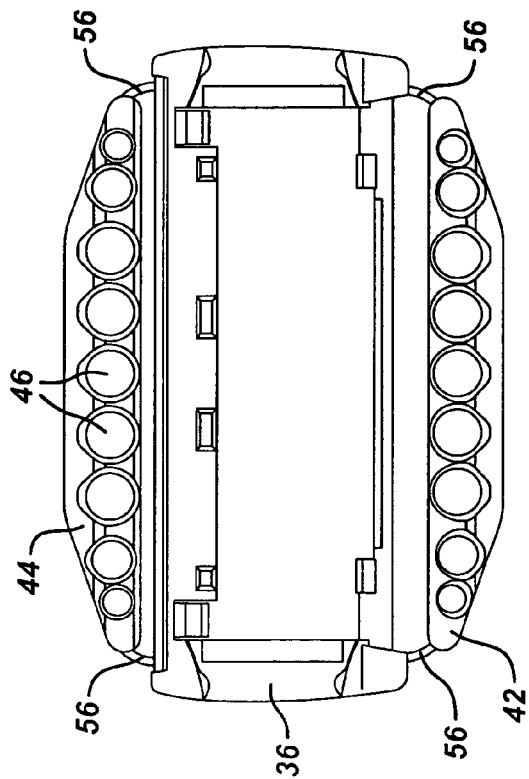
Figure 6C:
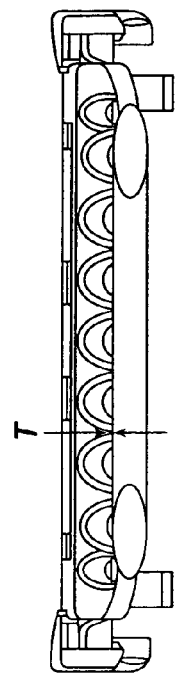

The elastomeric hinges may be overmolded onto the frame. To assist in this process, in the embodiment shown in FIGS. 5A-6D, the frame is connected to each of the wings by a pair of connecting members 56 that extend integrally from the frame to the wings (FIG. 6B). If desired, these connecting members may be cut after overmolding has been completed. Alternatively, the wings and frame may be separate components that are placed in an insert mold and overmolded with elastomer. Forming the hinges solely of elastomer (i.e., substantially free of rigid plastic) may result in a softer flexing hinge in some cases.

Contouring of Shaving Aid Portions

Referring to FIG. 4E, the front shaving aid portion 31A includes a ramped leading surface 33 that is contoured to cause the shaving aid portion to deflect upon skin contact, so that the cartridge will not rock back when shaving aid portion 31A contacts the skin during shaving. As can be seen in FIGS. 4A and 4D, a leading edge 110 of the shaving aid portion 31A has a first thickness t1 adjacent the side surfaces of the holder 30 and tapers to a second, lesser thickness t2 adjacent a center region of the shaving aid portion. This shape allows the front shaving aid portion to have the ramped leading surface 33, while still providing as much shaving aid as possible adjacent the side surfaces. If desired, the entire leading edge could have the lesser thickness t2. The front face 35 of the shaving aid portion 31A includes smoothly curved, arcuate side areas 37A, 37B, to enhance the soap-deflecting contour of leading surface 33 and to avoid edges and corners that could be uncomfortable during shaving and facilitate shaving of tight areas such as the underarm and behind the knee. Similarly, the intersections 39 of leading surface 33 and front face 35 are smoothly radiused.

Both the front shaving aid portion 31A and the rear shaving aid portion 31B are contoured so that the upper surface of each shaving aid portion (surface 41 of shaving aid portion 31A and surface 43 of shaving aid portion 31B) lies relatively flat against the user's skin when the wing 44 is deflected. This flat position, shown in FIG. 4F, allows as much shaving aid as possible to be in contact with the user's skin during shaving.

Ease of Shaving

Shaving aid portions 31A, 31B have a width W at their widest point (FIG. 4C) that is equal to or slightly less than the width of the frame 36 of the holder 30. Thus, the shaving aid portions do not extend beyond the side walls of the frame 36. As a result, the area around the side walls of the frame is unobstructed, allowing the shaver to determine, by sight and/or tactile sensation, what area has been shaved. If desired, the shaving aid portions may extend slightly beyond the side walls of the frame, e.g., by 2 mm or less on each side.

Shaving is also facilitated by rails 61 (FIGS. 4A, 5C), discussed above, which can engage the user's skin during shaving, potentially enhancing tracking of the cartridge.

While the embodiments described above have a pair of shaving aid portions, the razors can in the alternative have a single shaving aid portion, which can be located in front of the blades, behind the blades, or can extend completely around the blades.

EXAMPLES

The invention is further described in the following examples, which do not limit the scope of the invention described in the claims.

Example 1

Two control samples of a shaving aid composition were prepared, utilizing a generic commercially available poured soap base. The resistance to wear was determined by determining the number of shaves before a noticeable degradation in shaving performance, with the result identified as the "# shaves" in the tables set for the below. The formulations and results are set forth in Table 1:

TABLE 1

|  | Control 1 | Control 2 |
|---|---|---|
| Poured soap base | 68.35 | 72.33 |
| Hydroxyethylcellulose | 0.50 | 0.50 |
| Sodium stearate | 20.0 | 17.5 |
| C16-C17 alkyl benzoate | 5.0 | 4.0 |
| Kokum/Mango butter blend | — | 5.0 |
| Castoryl maleate | 5.0 | — |
| Titanium dioxide | 0.5 | — |
| Fragrance | 0.65 | 0.65 |
| Dye solution | — | 0.2 |
| Total | 100.0 | 100.0 |

Example 2

In this example, melt point and wear enhancers were added to a generic poured soap base and formulated into three different shaving aid compositions; one with no polyoxyethylene and two including differing quantities and molecular weight distributions of polyoxyethylene. The number of shaves before a noticeable degradation in shaving performance was determined, and wear testing was performed, in which the amount of shaving aid composition remaining after being subject to the wear test, expressed as a percentage, were determined. The wear test used throughout the examples of this specification involve the wet wheel method described above, using a loop portion of a hook-and-loop closure system as the abrasive surface; a wheel diameter of 10 inches; a wheel rotation speed of 10 rpm; a load of 200 g; 30 rotations of the wheel; and a shaving aid composition of 13.6 mm in width, 36.6 mm in length, 10 mm in height, and having a 5° taper from the center of the surface of contact to the edges of the surface of contact. The formulations and results are set forth in Table 2:

TABLE 2

|  | Sample A | Sample B | Sample C |
| --- | --- | --- | --- |
| Poured Soap Base | 67.97 | 66.47 | 62.97 |
| Sodium Stearate | 17.50 | 17.50 | 17.50 |
| Polyethylene/polybutene/mineral oil blend | 4 | 4 | 4 |
| Squalene and lauryl dimethicone/polyglycerin-3 crosspolymer | 3.33 | 3.33 | 3.33 |
| Tris (Tetramethylhydroxypiperidinol) Citrate and water and ethanol | 0.5 | 0.5 | 0.5 |
| Kokum Butter | 1 | 1 | 1 |
| Avocado Butter | 2 | 2 | 2 |
| Olive Butter | 2 | 2 | 2 |
| POLYOX ®, 1,000,000/4,000,000, 2:1 blend | — | 1.50 | — |
| POLYOX ®, 300,000/5,000,000, 1:2 blend | — | — | 5.00 |
| Polyquaternium-10 | 0.1 | 0.1 | 0.1 |
| Panthenol | 0.25 | 0.25 | 0.25 |
| Niacinamide | 0.25 | 0.25 | 0.25 |
| Dye & fragrance | 1.10 | 1.10 | 1.10 |
| % Wear | 51 | 62 | 80 |

As can be seen, the inclusion of the melt point and wear enhancers resulted in a greater number of shaves prior to degradation of shaving performance, as compared with Control Samples 1 and 2 from Example 1, as well as improving the wear characteristics of the composition. The addition of polyoxyethylene resulted in further improvement.

Example 3

Six samples of molded shaving aid compositions including polyoxyethylene were prepared and tested for wear under the same conditions as found in Example 2, as was a control sample having no polyoxyethylene. The formulations and results are set forth in Table 3:

TABLE 3

|  | Control 3 | Sample D | Sample E | Sample F | Sample G | Sample H | Sample I |
| --- | --- | --- | --- | --- | --- | --- | --- |
| Poured Soap Base | 67.97 | 66.47 | 66.30 | 62.97 | 66.97 | 62.97 | 62.97 |
| Tris (Tetramethylhydroxypiperidinol) Citrate and water and ethanol | 0.50 | 0.50 | 0.50 | 0.50 | 0.50 | 0.50 | 0.50 |
| Sodium Stearate | 17.50 | 17.50 | 17.50 | 17.50 | 17.50 | 17.50 | 17.50 |
| Polyethylene/polybutene/mineral oil blend | 4.00 | 4.00 | 4.00 | 4.00 | — | — | 4.00 |
| Squalene and lauryl dimethicone/polyglycerin-3 crosspolymer | 3.33 | 3.33 | — | 3.33 | 3.33 | 3.33 | 3.33 |
| C16-C17 alkyl benzoate | — | — | — | — | — | 4.00 | — |
| Olive, avocado, and kokum butter | 5.00 | 5.00 | 5.00 | 5.00 | 5.00 | 5.00 | 5.00 |
| Polyquaternium-10 | 0.10 | 0.10 | 0.10 | 0.10 | 0.10 | 0.10 | 0.10 |
| Vitamins | 0.50 | 0.50 | 0.50 | 0.50 | 0.50 | 0.50 | 0.50 |
| 1% dye solution | 0.1 | 0.10 | 0.10 | 0.10 | 0.10 | 0.10 | 0.10 |
| Fragrance (IFF 4473-BH) | 1.00 | 1.00 | 1.00 | 1.00 | 1.00 | 1.00 | 1.00 |
| Polyoxyethylene, 300k | — | — | — | — | — | — | 1.50 |
| Polyoxyethylene, 1 mil. | — | 1.00 | 5.00 | 5.00 | 5.00 | 4.00 | — |
| Polyoxyethylene, 4 mil. | — | 0.50 | — | — | — | 1.00 | — |
| Polyoxyethylene, 5 mil. | — | — | — | — | — | — | 3.50 |
| % Wear | 51 | 62 | 64 | 66 | 63 | 65 | 80 |

As can be seen, an increase in the quantity of polyoxyethylene results in an increased wear resistance in the molded shaving aid composition. Similarly, an increase in the molecular weight of the polyoxyethylene results in an increase in the wear resistance. Finally, the inclusion of both the polyethylene/polybutene/mineral oil blend and a silicone cross-polymer (sample F) results in a molded shaving aid composition having a greater wear resistance than that of a molded shaving aid composition having only one of the polyethylene/polybutene/mineral oil blend and a silicone cross-polymer (samples E and G).

Example 4

Two samples of a molded shaving aid composition were prepared using a commercially available poured soap base, and tested for wear using the same conditions as in Examples 1 and 2. One sample included a silicone cross-polymer, with the other sample serving as a control:

TABLE 4

|  | Control 4 | Sample J |
| --- | --- | --- |
| Poured soap base | 71.30 | 67.97 |
| Sodium Stearate | 17.50 | 17.50 |
| Polyethylene/polybutene/mineral oil blend | 4 | 4 |
| Tris (Tetramethylhydroxypiperidinol) Citrate and water and ethanol | 0.5 | 0.5 |

TABLE 4-continued

|  | Control 4 | Sample J |
| --- | --- | --- |
| Olive, avocado, and kokum butter | 5.00 | 5.00 |
| Polyquaternium-10 | 0.1 | 0.1 |
| Vitamins | 0.50 | 0.50 |
| Moisturizer components | 0.60 | 0.60 |
| Silicone cross-polymer | — | 3.33 |
| Dye and fragrance | 1.10 | 1.10 |
| Wear Data | 42% | 51% |

As can be seen, the inclusion of a silicone cross-polymer results in an increase in the wear resistance of the molded shaving aid composition.

Example 5

In this example, a poured soap base was created and melt-point and wear enhancers, as well as other shaving aid components were added. The samples were tested for wear under the same conditions as used in Example 2:

TABLE 5

|  | Sample K | Sample L | Sample M |
| --- | --- | --- | --- |
| Dipropylene Glycol | 23.55 | 14.00 | 13.50 |
| Water | 9.75 | — | — |
| Sorbitol | 8.00 | — | — |
| Glycerin | 8.00 | 29.00 | 25.90 |
| Behenyl Alcohol | — | — | 1.10 |
| Stearic Acid | — | 3.00 | — |
| Microcrystalline Wax | — | 1.00 | 0.50 |
| Cocamidopropyl Betaine | — | 6.00 | 11.00 |
| Sodium Lauryl Ether Sulfate | 8.00 | 12.00 | 6.00 |
| Steareth-21 | — | — | 5.00 |
| Methocel | — | — | 1.00 |
| Tetramethylhydroxypiperidinol Citrate | 0.50 | — | — |
| Sodium Stearate | 30.00 | 28.00 | 30.00 |
| Polybutene/polyethylene/mineral oil | 4.00 | — | — |
| Olive, avocado and kokum butter | 5.00 | — | — |
| Shea butter | — | 1.00 | 1.00 |
| Vinyl dimethicone/methicone silsesquioxane cross-polymer | 1.00 | — | — |
| Polyquaternium-10 | 0.10 | — | — |
| Vitamins | 0.50 | — | — |
| POLYOX ® (MW = 300,000) | — | — | 0.50 |
| POLYOX ® (MW = 1,000,000) | 0.50 | — | — |
| POLYOX ® Coagulant (MW = 5,000,000) | — | 5.00 | 3.50 |
| Dye and Fragrance | 1.1 | 1.1 | 1.1 |
| % Wear | 62 | 79 | 70 |

As can be seen, a higher level of polyoxyethylene and/or a higher molecular weight distribution of polyoxyethylene resulted in improved wear characteristics.

Example 6

A poured soap base was made, and a shaving aid composition was formulated using the poured soap base, and tested for wear using the same conditions as in Example 2. The composition of the shaving aid composition is set forth in Table 6:

TABLE 6

|  | Sample X |
| --- | --- |
| Dipropylene glycol | 14.0 |
| Glycerin | 28.9 |
| Stearic acid | 3.00 |
| Microcrystalline wax | 1.00 |
| Cocamidopropyl betaine | 6.00 |
| Sodium lauryl ether sulfate, 25% active | 12.0 |
| Sodium stearate | 28.0 |
| Shea butter | 1.00 |
| Polyoxyethylene, 5 mil. | 5.00 |
| 1% dye solution & fragrance | 1.1 |

While embodiments above are directed to a molded shaving aid composition that is incorporated into a razor, the shaving aid composition can utilized as a stand-alone shaving aid. For example, the shaving aid composition can be molded into a bar that is applied to the skin just prior to shaving, much as a bar of soap is used. The shaving aid composition can be applied with a brush, in the form of a shaving soap. The shaving aid composition can be utilized as a soap bar for cleaning and/or exfoliating skin.

As another example, while particular cartridges have been discussed above, the shaving aid holder may be used with any desired type of cartridge, or may be used with a razor having a razor blade unit that is unitary with the razor handle. If a different cartridge shape is used, the shape of the frame of the shaving aid holder and/or the dimensions of the shaving aid holder may be adjusted accordingly.

Additionally, while the wings described above include apertures to secure the shaving aid in place, solid wings may be used if the shaving aid exhibits adequate adhesion to the wings or is attached to the wings in a different manner. Also, while the flexible hinges described above are formed of an elastomeric material, in some cases the hinges may be formed of rigid plastic, e.g., "living hinges."

In some embodiments, the cartridge may include a cap with a lubricating strip, e.g., mounted in a slot at the rear of the cartridge housing. The lubricating strip may be made of a material comprising a mixture of a hydrophobic material and a water leachable hydrophilic polymer material, as is known in the art and described, e.g., in U.S. Pat. Nos. 5,113,585 and 5,454,164, which are hereby incorporated by reference.

All documents cited in the Detailed Description of the Invention are, in relevant part, incorporated herein by reference; the citation of any document is not to be construed as an admission that it is prior art with respect to the present invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated hereby by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A shaving cartridge comprising:
a housing having a front edge and a rear edge;
one or more shaving blades between the front edge and the rear edge;
a shaving aid holder; and/
at least one shaving aid portion mounted on the shaving aid holder, the shaving aid portion comprising from 0.25 wt % to 5 wt % silicone cross-polymer, from 10 wt % to 60 wt % sodium stearate as a soap base, from 0.5 wt % to 8 wt % semi-solid esters, from 0.25 wt % to 10 wt % polyoxyethylene, and from 0.3 wt % to 10 wt % of a polyethylene, polybutene and mineral oil composition.

2. The shaving cartridge of claim 1, wherein the polyoxyethylene has a molecular weight of from about 100,000 to about 5,000,000.

3. The shaving cartridge of 1 wherein the silicone crosspolymer is selected from the group consisting of dimethicone PEG-7 panthenyl phosphate, dimethicone PEG-7 phosphate, dimethicone PEG-7 undecylenate, dimethicone/methicone copolymer, perfluoronoylethyl dimethicone methicone copolymer, dimethicone/vinyl dimethicone crosspolymer in dimethicone, vinyl dimethicone/lauryl dimethicone crosspolymer in mineral oil, vinyl dimethicone/lauryl dimethicone crosspolymer in squalane, vinyl dimethicone/methicone silsesquioxane crosspolymer, squalene and lauryl dimethicone/polyglycerin-3 crosspolymer, triethylhexanoin and lauryl dimethicone/polyglycerin-3 crosspolymer, and dimethicone/polyglycerin-3 crosspolymer and dimethicone, PEG/PPG-20/6 dimethicone, behenoxydimethicone, C24-28 alkyl methicone, dimethicone/vinyl dimethucine crosspolymer, and C12-C14 Pareth-12.

4. The shaving cartridge of claim 1, wherein the soap base is a poured soap base.

5. The shaving cartridge of claim 1, wherein the soap base is an extruded soap base.

* * * * *